(12) United States Patent
Park et al.

(10) Patent No.: US 7,981,385 B2
(45) Date of Patent: Jul. 19, 2011

(54) MICROFLUIDIC DEVICE AND MICROFLUIDIC SYSTEM WITH THE SAME

(75) Inventors: Jong-myeon Park, Seoul (KR); Jeong-gun Lee, Seoul (KR); Jung-suk Yoo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 147 days.

(21) Appl. No.: 12/114,214

(22) Filed: May 2, 2008

(65) Prior Publication Data

US 2008/0274015 A1    Nov. 6, 2008

(30) Foreign Application Priority Data

May 3, 2007    (KR) .................. 10-2007-0043026

(51) Int. Cl.
*B01L 3/00*    (2006.01)
(52) U.S. Cl. ........ 422/537; 422/502; 422/506; 422/500; 422/68.1; 422/72
(58) Field of Classification Search .............. 422/68.1, 422/72, 100, 103
See application file for complete search history.

(56) References Cited

U.S. PATENT DOCUMENTS

| | | | | |
|---|---|---|---|---|
| 6,063,589 | A * | 5/2000 | Kellogg et al. | 422/68.1 |
| 7,599,275 | B2 * | 10/2009 | Worthington et al. | 422/72 |
| 2003/0156991 | A1 * | 8/2003 | Halas et al. | 422/100 |
| 2004/0007275 | A1 | 1/2004 | Hui Liu et al. | |
| 2004/0196569 | A1 * | 10/2004 | Quake et al. | 359/656 |
| 2005/0164158 | A1 * | 7/2005 | Wang et al. | 435/2 |
| 2008/0058192 | A1 * | 3/2008 | Cho et al. | 494/1 |

FOREIGN PATENT DOCUMENTS

WO    99/44217    9/1999

OTHER PUBLICATIONS

Park et al. "Multifunctional microvalves control by optical illumination on nanoheaters and its application in centrifugal microfluidic devices" Lab on a Chip, Royal Society of Chemistry, vol. 7, Feb. 2007, pp. 557-564.

* cited by examiner

*Primary Examiner* — In Suk Bullock
*Assistant Examiner* — Sharon Pregler
(74) *Attorney, Agent, or Firm* — Sughrue Mion, PLLC

(57) ABSTRACT

Provided is a microfluidic device and microfluidic system with the device. The microfluidic device includes a substrate; a channel formed in the substrate and in which a fluid can move; a valve controlling flow of a fluid flowing along the channel and including a phase transition material which can be melted by energy such as electromagnetic wave energy; and a lens disposed on the substrate and adjusting an irradiating region of the valve, onto which the energy is applied.

19 Claims, 4 Drawing Sheets

MICROFLUIDIC DEVICE AND MICROFLUIDIC SYSTEM WITH THE SAME

CROSS-REFERENCE TO RELATED PATENT APPLICATION

This application claims the benefit of Korean Patent Application No. 10-2007-0043026, filed on May 3, 2007, in the Korean Intellectual Property Office, the disclosure of which is incorporated herein in its entirety by reference.

BACKGROUND OF THE INVENTION

1. Field of the Invention

The present invention relates to microfluidics, and more particularly, to a microfluidic device and microfluidic system including the microfluidic device.

2. Description of the Related Art

Conventionally, a microfluidic device has structures such as a chamber storing a minute amount of fluid, a channel through which the fluid flows, a valve for controlling flow of the fluid, and various functional units receiving the fluid to perform predetermined functions thereon. A biochip is obtained by arranging the structures on a chip-type substrate and is used to analyse the performance of various assays including biologic reactions. In particular, a device that is designed to perform multiple step processes and manipulations in a single chip is referred to as a lab-on-a chip.

A driving pressure is generally required to transfer the fluid within a microfluidic device. Capillary pressure or a pressure generated by a specifically prepared pump is used as the driving pressure. A lab compact disk (CD) or a lab-on a disk is a recently-suggested microfluidic device obtained by arranging microfluidic structures on a compact disk-shaped platform and uses centrifugal force. This is referred to as a lab CD or a lab-on a disk.

Each of microfluidic devices for biochemistry reactions, which are disclosed in pages 1824-1831 and 3740-3748, Anal. Chem. Vol. 76 published on 2004, includes a valve formed of only paraffin wax, and a heater for melting the paraffin wax. However, since a quite large amount of paraffin wax is needed for closing a channel, and a heater having large capacity is required for melting the quite large amount of paraffin wax, it is difficult to miniaturize the microfluidic devices and integrate them into an existing microfluidic systems. In addition, it takes a long time for the paraffin wax to be melted, and it is difficult to minutely control a point of time at which a channel is opened.

SUMMARY OF THE INVENTION

According to an aspect of the present invention, there is provided a microfluidic device including: a substrate; a channel formed in the substrate and in which a fluid can move; a valve which controls flow of a fluid flowing along the channel and comprising a phase transition material which is in a non-fluidic phase at an ambient temperature and changes into a fluid phase upon application of energy; and a lens which is disposed on the substrate and adjusts a beam of the energy applied from an energy source to the valve.

The valve may be located in the channel to close the channel, and, may be melted to open the channel when energy, such as electromagnetic wave is applied to the valve.

The device may further include a chamber for housing the valve, and the valve may be disposed in the chamber, wherein the valve may be melted to flow into the channel, when energy is applied to the valve and may be hardened in the channel to close the channel.

The lens may be detachably attached to a surface of the substrate or may be integrally formed on the substrate.

The lens may be disposed between the energy source and the valve closing the channel, and the lens concentrates the energy applied to the valve.

The lens may be disposed between the energy source and the valve contained in the chamber, and the lens diverges the energy applied to the valve.

The device may have a first lens and a second lens, wherein the first lens is disposed between the energy source and the valve closing the channel, and wherein the first lens concentrates the energy applied from the energy source to the valve closing the channel, and wherein the second lens is disposed between the energy source and the valve contained in the chamber, and the second lens diverges the energy applied from the energy source to the valve contained in the chamber.

The valve may include a plurality of minute heating particles that are diffused in the phase transition material and each absorb electromagnetic wave energy to emit heat.

The minute heating particles may be are mixed with the phase transition material in a state in which the minute heating particles are diffused in water-repellant carrier oil.

Each of the minute heating particles may be a minute metal oxide particle.

The minute metal oxide particle may include at least one selected from the group consisting of $Al_2O_3$, $TiO_2$, $Ta_2O_3$, $Fe_2O_3$, $Fe_3O_4$ and $HfO_2$.

Each of the minute heating particles may be a polymer particle, a quantum dot or a magnetic bead.

The phase transition material may be wax, gel or thermoplastic resin.

The wax may be at least one selected from the group consisting of paraffin wax, microcrystalline wax, synthetic wax and natural wax.

The gel may be at least one selected from the group consisting of polyacrylamide, polyacrylates, polymethacrylates and polyvinylamides.

The thermoplastic resin may be at least one selected from the group consisting of COC (cyclic olefin copolymer), PMMA (polymethylmethacrylate), PC (polycarbonate), PS (polystyrene), POM (polyoxymethylene), PFA (perfluoralkoxy), PVC (polyvinylchloride), PP (polypropylene), PET (polyethylene terephthalate), PEEK (polyetheretherketone), PA (polyamide), PSU (polysulfone) and PVDF (polyvinylidene fluoride).

The microfluidic device may further include a chamber formed in the substrate and housing a fluid.

According to another aspect of the present invention, there is provided a microfluidic system comprising the microfluidic device and an energy source formed with a distance from the substrate and irradiating energy (e.g., electromagnetic waves) to the valve.

The energy source may include a laser light source emitting laser light.

The microfluidic system may further include a motor rotating the substrate in order to apply a fluid driving pressure based on a centrifugal force to the substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Figure 1:
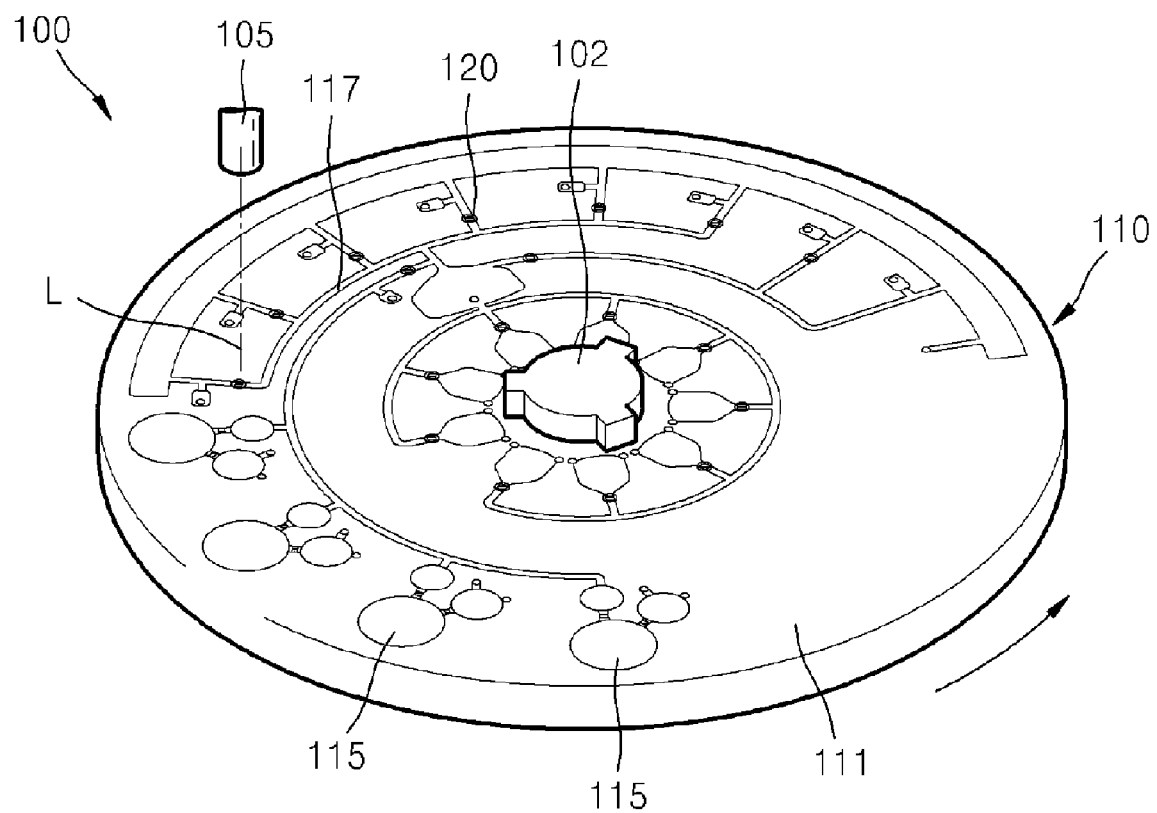
FIG. 1 is a perspective view of a microfluidic system according to an embodiment of the present invention.
Figure 2:
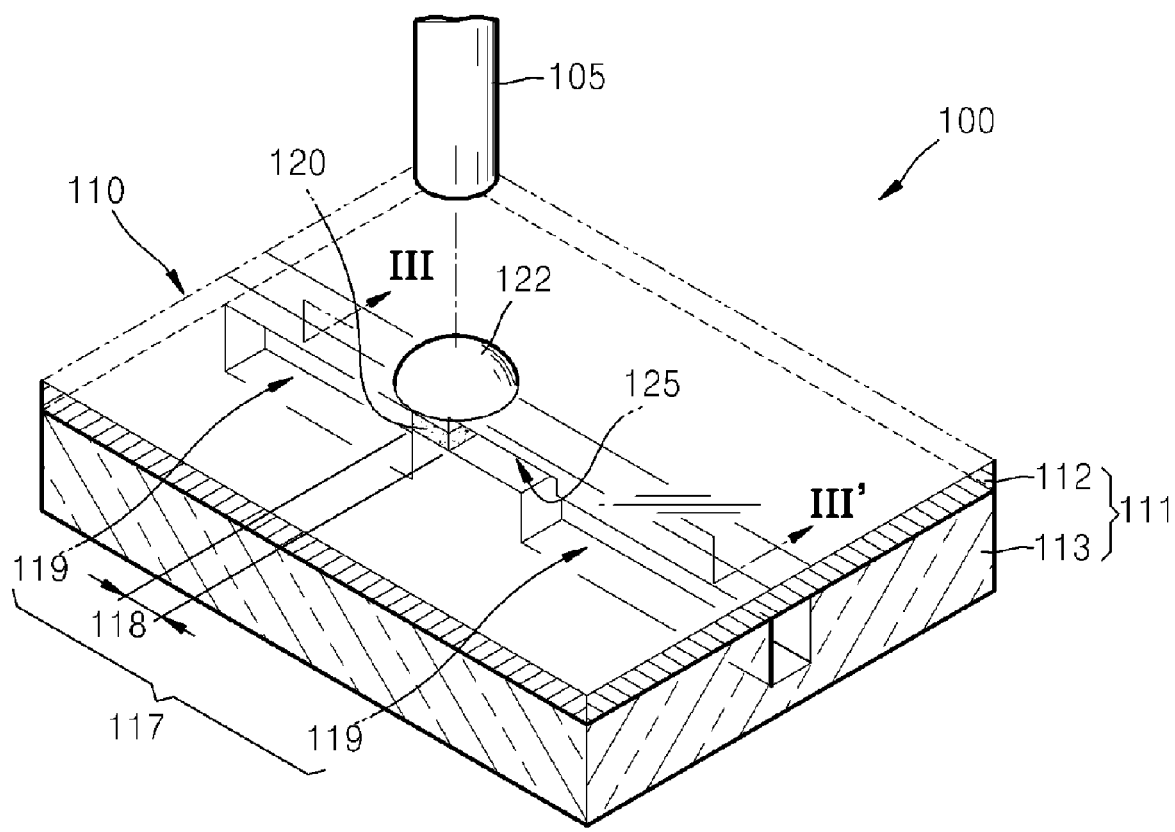
FIG. 2 is a partially enlarged perspective view of the microfluidic system of FIG. 1.
Figure 3:
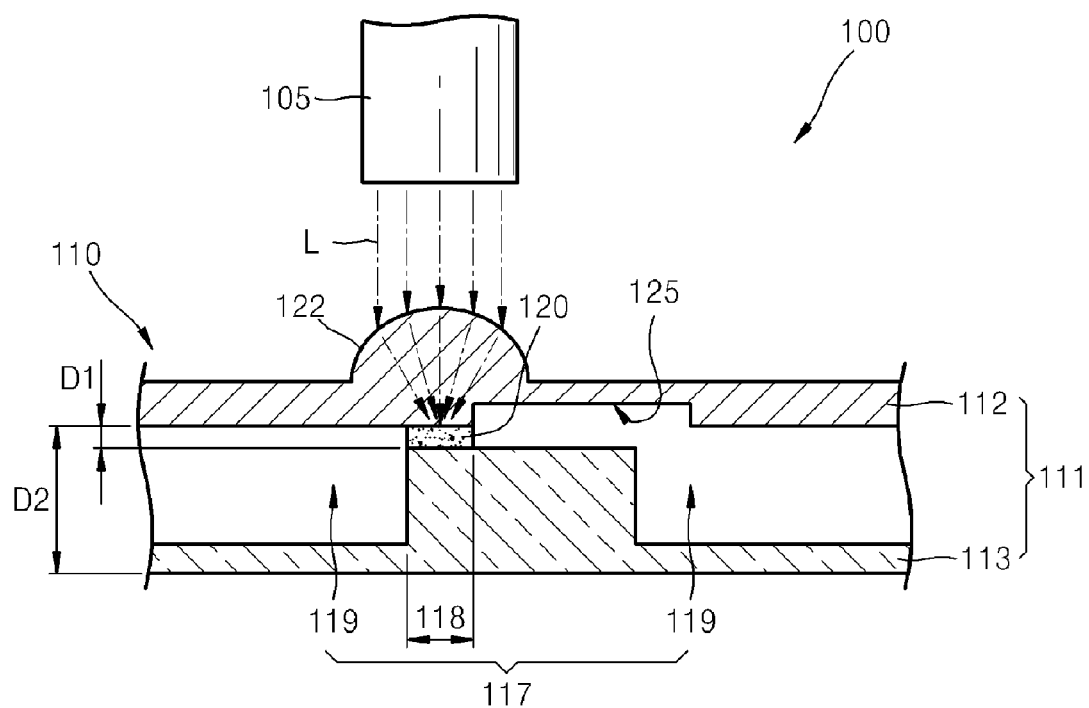
FIG. 3 is a longitudinal cross-sectional view of the microfluidic system taken along a line III-III' of FIG. 2.

FIG. 1 is a perspective view of a microfluidic system 100 according to an embodiment of the present invention. FIG. 2 is a partially enlarged perspective view of the microfluidic system 100 of FIG. 1. FIG. 3 is a longitudinal cross-sectional view of the microfluidic system 100 taken along a line III-III' of FIG. 2.

Referring to FIG. 1, the microfluidic system 100 includes a microfluidic device 110 including a rotatable disk-type substrate 111, a spindle motor 102 for supporting and rotating the microfluidic device 110, and an energy source 105. In the embodiment shown in FIG. 1, the energy source 105 is a laser light source 105 and is located with distance from the substrate 111.

The microfluidic device 110 includes a chamber 115 for housing a fluid in the substrate 110, a channel 117 for moving a fluid, and a valve 120 for controlling flows of fluid moving along the channel 117. In the microfluidic device 110, the chamber 115, the channel 117 and the valve 120 are arranged according to intended functions of biochemical field (e.g., centrifugal separation of a fluid sample, an immunoassay, gene analysis or the like). That is, the microfluidic device 110 is not limited to the arrangement shape of the chamber 115, the channel 117 and the valve 120 that are illustrated in FIG. 1. That is, the microfluidic device 110 can be designed to have various arrangements and/or shapes of the structure according to the desired use of the microfluidic device.

The spindle motor 102 rotates the microfluidic device 110 in order to apply a driving pressure based on a centrifugal force to a fluid remaining in the chamber 115 or channel 117 of the microfluidic device 110. The fluid remaining in the microfluidic device 110 is pushed towards a circumference of the substrate 111 due to the rotation of the spindle motor 102.

The laser light source 105 is an example of an energy source for emitting magnetic waves to the valve 120, and projects a laser light L, which is a kind of electromagnetic wave, towards the valve 120 of the microfluidic device 110 to provide energy to the valve 120. The laser light source 105 may include a laser diode (LD). The valve 120 absorbs electromagnetic wave energy, which is provided in the form of the laser light L, and changes into a fluidic phase (e.g., melted).

Referring to FIGS. 2 and 3, the valve 120 is referred to as a 'normally closed valve' which closes the channel 117 so that a fluid may not flow before the valve 120 changes into a fluidic phase by, for example, absorbing electromagnetic wave energy. The valve 120 includes a phase transition material that is melted by electromagnetic wave energy, and a plurality of minute heating particles that are diffused in the phase transition material and absorb electromagnetic wave energy to emit heat.

The phase transition material may be wax. When the wax is heated, the wax is melted to change into a liquid state and volume expansion of the wax occurs. For example, the wax may be paraffin wax, microcrystalline wax, synthetic wax or natural wax.

Meanwhile, the phase transition material may be gel or thermoplastic resin. The gel may be polyacrylamide, polyacrylates, polymethacrylates or polyvinylamides. The thermoplastic resin may be cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), PVDF (polyvinylidene fluoride) or the like.

Minute heating particles have a diameter in the range of 1 nm to 100 μm so as to freely pass through the minute channel 117, which usually have a depth of about 0.1 mm and a width of about 1 mm. The minute heating particles, which may be employed in the present invention, are characterized that the temperature of minute heating particles is remarkably increased to emit heat when electromagnetic wave energy is provided using laser light L irradiation and the minute heating particles are evenly diffused in the phase transition material. To achieve these properties, the minute heating particle may include a core including a metal component and a hydrophobic surface structure. For example, the minute heating particle may include a core formed of Fe, and a shell surrounding Fe core, the shell includes a plurality of surfactant components combined with Fe.

Usually, the minute heating particles are kept in a state in which the minute heating particles are diffused in carrier oil. The carrier oil may also be hydrophobic so that the minute heating particle including the hydrophobic surface structure may be evenly or homogenously dispersed in the carrier oil. By pouring and mixing the carrier oil, in which the minute heating particles are dispersed, with the melted phase transition material, a valve forming material for forming the valve 120 can be manufactured.

The minute heating particles are not limited to polymer particles, of which exemplary list is described above. That is, the minute heating particles may be a form of quantum dots or magnetic beads. For example, the minute heating particles may be minute metal oxide particles such as $Al_2O_3$, $TiO_2$, $Ta_2O_3$, $Fe_2O_3$, $Fe_3O_4$, or $HfO_2$. Meanwhile, the valve 120 may not necessarily include the minute heating particles. That is, the valve 120 may be formed of only the phase transition material without the minute heating particles.

The substrate 111 includes an upper plate 112 and a lower plate 113 that are bonded each other. The upper plate 112 and the lower plate 113 can be bonded using supersonic fusion, or by interposing double-sided adhesive tape therebetween. The upper plate 112 and the lower plate 113 may be fabricated using injection molding of thermoplastic resin.

When the microfluidic system 100 includes the laser light source 105 disposed above the microfluidic device 110, the laser light L passes through the upper plate 112 to be incident to the valve 120. Accordingly, at least the upper plate 112 may be transparent such that electromagnetic waves may easily pass through the upper plate 112. Meanwhile, the microfluidic device 110 includes a means 122 for concentrating the energy applied to the valve 120. For example, a convex lens 122 which focuses (or concentrates) the laser light L projected from the laser light source 105 towards the valve 120 may be used to enhance melting of the valve 120 and prevent incomplete melting of the valve 120. The convex lens 122 is formed on a portion of the substrate 111, which covers the location of the valve 120. The convex lens 122 may be integrally formed on the upper plate 112 using injection molding of thermoplastic resin. One or both of the surfaces of the lens 122 may convex. However, the present invention is not limited to the microfluidic device 110 including the upper plate 112 having the convex lens 122 integrally formed thereon. That is, a microfluidic device according to the present invention may include a lens detachably attached onto a substrate. In addition, the present invention may include a microfluidic system in which an energy source is disposed below a microfluidic device, and accordingly a lens is disposed on a lower plate.

The channel 117 comprises a first area 118 of a first dimension D1 in a portion and a pair of second areas 119 adjacent to the first area 118. The second areas 119 are of a second dimension D2 which is greater than D1. The microfluidic device 110 includes a valve forming material housing unit 125 that is formed on a portion that is connected to the channel 117 and is not in the channel 117. In particular, the valve forming material housing unit 125 is formed on a lower surface of the upper plate 112 in the form of a groove. A melted valve forming material M is injected into the valve forming material housing unit 125 to be hardened. When the valve forming material is melted by energy, such as heat, applied to the valve, the melted valve forming material flows and remains in the first area 118 due to capillary force. The valve forming material remaining in the first area 118 hardens into a solid state at room temperature, thereby closing the channel 117. When the laser light L is irradiated to the valve 120 closing the channel 117 using the laser light source 105 for a period of time, the minute heating particles included in the valve 120 rapidly emit heat to rapidly heat the phase transition material. Thus, the valve 120 is rapidly melted. The channel 117 becomes open, and flow of a fluid along the channel 117 can occur. Referring to FIG. 3, since the convex lens 122 condenses the laser light L projected from the laser light source 105 to the valve 120 in the microfluidic system 100, operational errors due to imperfect meting of a part of the valve 120, in which the channel 117 is not completely opened, are prevented. Since the laser light L is condensed to the valve 120, although the laser light source 105 having relatively low output is used, reliable operation of the valve 120 can be ensured. Since a lens and a barrel are not necessary to be equipped in the laser light source 105, and the convex lens 122 is integrally formed on the upper plate 112 using injection molding, the manufacturing costs of the microfluidic system 100 can be reduced.

Figure 4:
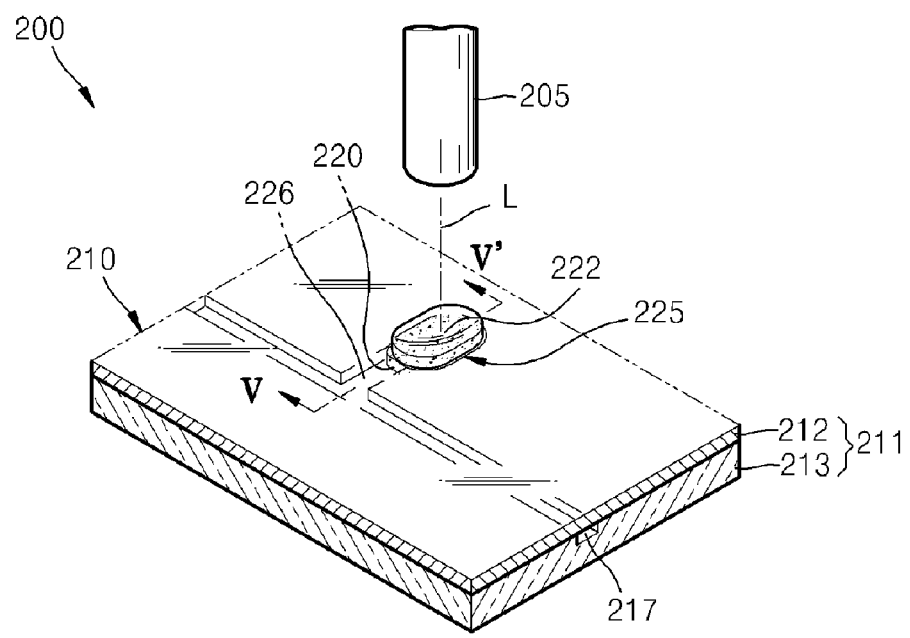
FIG. 4 is a partially perspective view of a microfluidic system according to another embodiment of the present invention.
Figure 5:
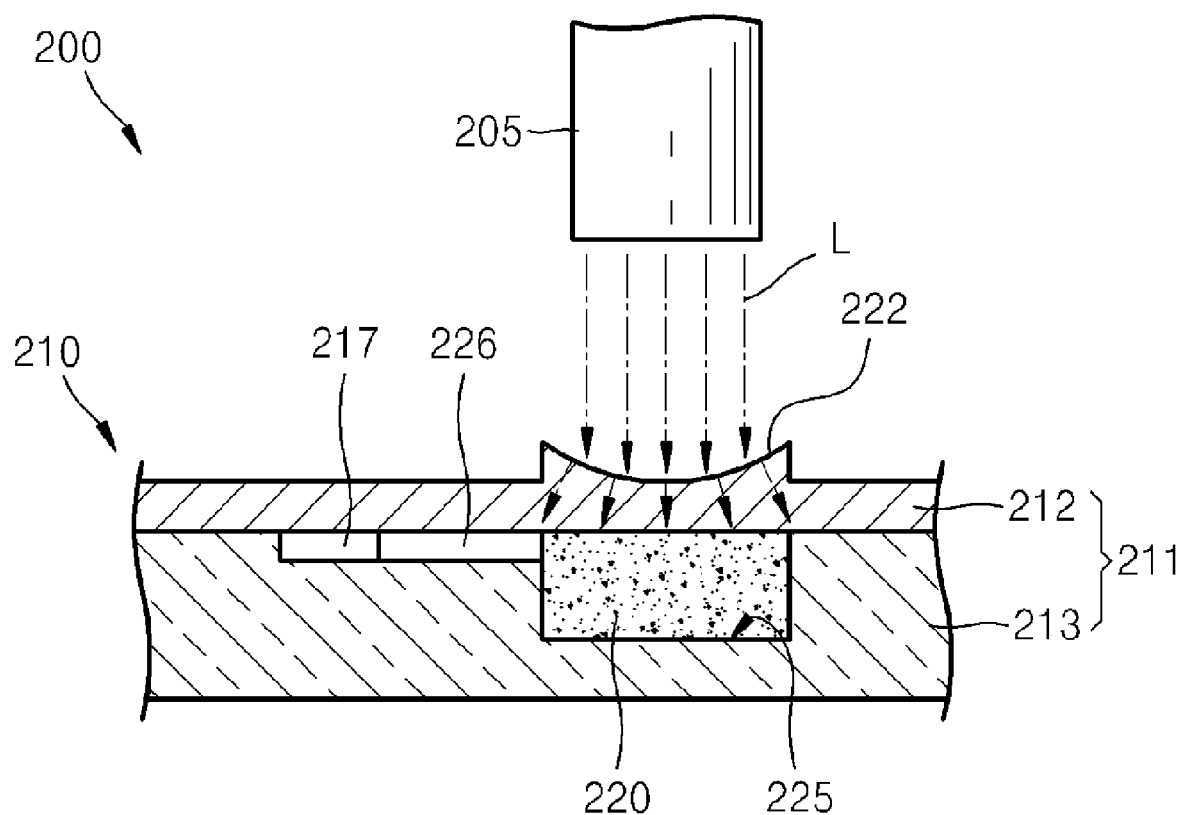
FIG. 5 is a longitudinal cross-sectional view of the microfluidic system taken along a line V-V' of FIG. 4.

FIG. 4 is a partially perspective view of a microfluidic system 200 according to another embodiment of the present invention. FIG. 5 is a longitudinal cross-sectional view of the microfluidic system 200 taken along a line V-V' of FIG. 4.

Referring to FIGS. 4 and 5, the microfluidic system 200 includes a microfluidic device 210, and a laser light source 205 spaced from the microfluidic device 210. The microfluidic device 210 includes a substrate 211, a channel 217 formed in the substrate 211, and a valve 220 for controlling flow of a fluid flowing along the channel 217.

The valve 220 does not close the channel 217 before the valve 220 absorbs electromagnetic wave energy. However, when the valve 220 absorbs electromagnetic wave energy, the valve 220 closes the channel 217. Thus, the valve 220 is referred to as a 'normally opened valve.' The valve 220 includes a phase transition material, and a plurality of minute heating particles that are diffused in the phase transition material and absorb electromagnetic wave energy to emit heat. The valve 220 and a valve forming material for forming the valve 220 are respectively the same as the valve 120 and the valve forming material of the microfluidic system 100 of FIGS. 2 and 3, described above, and thus their descriptions will be omitted.

The substrate 211 is formed by bonding an upper plate 212 and a lower plate 213. The upper plate 212 and the lower plate 213 can be bonded using supersonic fusion, or by interposing double-sided adhesive tape therebetween. The upper plate 212 and the lower plate 213 can be fabricated using injection molding of thermoplastic resin. A valve chamber 225 and a connection unit 226 are disposed in the substrate 211, wherein the valve chamber 225 is disposed around the channel 217 and the connection unit 226 connects the valve chamber 225 to the channel 217. The valve chamber 225 houses the valve 220. In the microfluidic device 210 of FIGS. 4 and 5, the channel 217, the valve chamber 225 and the connection unit 226 are formed on the lower plate 213. However, the present invention is not limited to the structure shown in the drawings. That is, at least one of a channel, a valve chamber and a connection unit may be formed on an upper plate.

The valve 220 occupies a relatively large area of the substrate 211 unlike the valve 120 illustrated in FIGS. 2 and 3. Accordingly, when a cross sectional area of the light emitted by the laser light source 205 is smaller than the occupying area of the valve 220 (for example, the case where the laser light source 205 includes a laser diode), the valve 220 may be partially melted to cause operation errors of the valve 220. The microfluidic device 210 includes a means for diverging energy beam applied to the valve 220. For example, concave lens 222 radiating a laser light L projected from the laser light source 205 may be used in order to prevent the operational errors of the valve 220. The concave lens 222 is formed on a portion of the substrate 211, which overlaps the valve 220. The concave lens 222 is integrally formed on the upper plate 212 using injection molding of thermoplastic resin. However, the present invention is not limited to the microfluidic device 210 including the upper plate 212 having the concave lens 222 integrally thereon. That is, a microfluidic device according to the present invention may include a lens detachably attached onto a substrate. In addition, the present invention may include a microfluidic system in which an energy source is disposed below a microfluidic device, and accordingly a lens is disposed on a lower plate.

When the laser light L is irradiated to the valve 220 using the laser light source 205 for a period of time, the minute heating particles included in the valve 220 rapidly emit heat to rapidly heat the phase transition material. Thus, the valve 220 is rapidly melted and expanded. The valve 220 flows into the channel 217 through the connection unit 226. The valve 220 is hardened in the channel 217 to close the channel 217. Referring to FIG. 6, since the concave lens 222 diverges the laser light L projected from the laser light source 205 such that the laser light L may be incident on an entire area of the valve 220 in the microfluidic system 200, operational errors due to imperfect melting of a part of the valve 220, in which the channel 217 is not completely opened, are prevented. Accordingly, the number of laser diodes required for configuring the laser light source 205 can be reduced. Since a lens and a barrel are not necessary to be equipped in the laser light source 205, and the concave lens 222 is integrally formed on the upper plate 212 using injection molding, the manufacturing costs of the microfluidic system 200 can be reduced.

The microfluidic device 210 may have a convex lens and a concave lens, wherein the convex lens is disposed between the energy source and the valve contained in the channel, and wherein the lens concentrates the beam of the energy and wherein the concave lens is disposed between the energy source and the valve contained in the chamber, and wherein the lens diverges the beam of the energy The microfluidic device 210 is fabricated using a method including preparing the lower plate 213 having the channel 217, the connection unit 226 and the valve chamber 225, and the upper plate 212 having the concave lens 222, forming the valve 220 by injecting the valve forming material into the valve chamber 225 of the lower plate 213 to be hardened, and bonding the upper plate 212 and the lower plate 213 so that a lower surface of the upper plate 212 and an upper surface of the lower plate 213 may face each other. In the bonding operation, supersonic fusion or double-sided adhesive tape can be used.

According to a microfluidic system according to the present invention, a valve included in the microfluidic system closes or opens a channel by irradiating electromagnetic waves, and thus the valve having short response time can be embodied.

A lens is provided on a substrate, and thus errors of controlling flow of a fluid, which are generated when a valve is partially melted, can be prevented. In addition, by forming a lens on a substrate, a lens and a barrel are not required for an energy source emitting electromagnetic waves. Accordingly, the manufacturing costs can be reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device comprising:
   a substrate, wherein the substrate includes an upper plate and a lower plate bonded to each other;
   a channel formed in the substrate and in which a fluid can move;
   a valve controlling flow of a fluid flowing along the channel and comprising a phase transition material which is in a non-fluidic phase at an ambient temperature and changes into a fluid phase upon application of energy; and
   a lens disposed on the substrate over top of the phase transition material and adjusts a beam of the energy applied from an energy source to the valve,
   wherein the lens is formed as an integral part of the upper plate or the lower plate and located on the exterior surface of the upper plate or the lower plate.

2. The microfluidic device of claim 1, wherein the valve is hardened in the channel to close the channel, and absorbs the electromagnetic wave energy to be melted to open the channel.

3. The microfluidic device of claim 1, wherein the valve is disposed around the channel so as to flow into the channel, absorbs the electromagnetic wave energy to be melted to flow into the channel, and is hardened in the channel to close the channel.

4. The microfluidic device of claim 1, wherein the lens is attached to a surface of the substrate or is integrally formed on the substrate.

5. The microfluidic device of claim 1, wherein the location of the lens overlaps the location of the valve.

6. The microfluidic device of claim 1, wherein the lens is a convex lens converging electromagnetic waves or a concave lens diverging electromagnetic waves.

7. The microfluidic device of claim 1, wherein the valve comprises a plurality of minute heating particles that are diffused in the phase transition material and each absorb electromagnetic wave energy to emit heat.

8. The microfluidic device of claim 7, wherein the minute heating particles are mixed with the phase transition material in a state in which the minute heating particles are diffused in water-repellant carrier oil.

9. The microfluidic device of claim 7, wherein each of the minute heating particles is a minute metal oxide particle.

10. The microfluidic device of claim 9, wherein the minute metal oxide particle comprises at least one selected from the group consisting of $Al_2O_3$, $TiO_2$, $Ta_2O_3$, $Fe_2O_3$, $Fe_3O_4$ and $HfO_2$.

11. The microfluidic device of claim 7, wherein each of the minute heating particles is a polymer particle, a quantum dot or a magnetic bead.

12. The microfluidic device of claim 1, wherein the phase transition material is wax, gel or thermoplastic resin.

13. The microfluidic device of claim 12, wherein the wax is at least one selected from the group consisting of paraffin wax, microcrystalline wax, synthetic wax and natural wax.

14. The microfluidic device of claim 12, wherein the gel is at least one selected from the group consisting of polyacrylamide, polyacrylates, polymethacrylates and polyvinylamides.

15. The microfluidic device of claim 12, wherein the thermoplastic resin is at least one selected from the group consisting of cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU) and polyvinylidene fluoride (PVDF).

16. The microfluidic device of claim 1, further comprising a chamber formed in the substrate and housing a fluid.

17. A microfluidic system comprising:
   a microfluidic device comprising:
      a substrate, wherein the substrate includes an upper plate and a lower plate bonded to each other;
      a channel formed in the substrate and in which a fluid can move;
      a valve which controls flow of a fluid flowing along the channel and comprising a phase transition material which is in a non-fluidic phase at an ambient temperature and changes into a fluid phase upon application of energy; and
      a lens disposed on the substrate over top of the phase transition material and adjusts a beam of the energy applied from an energy source to the valve,
      wherein the lens is formed as an integral part of the upper plate or the lower plate and located on the exterior surface of the upper plate or the lower plate; and
      an energy source which is disposed with a distance from the substrate and applies energy to the valve.

18. The microfluidic system of claim 17, wherein the energy source comprises a laser light source emitting laser light.

19. The microfluidic system of claim 17, further comprising a motor rotating the substrate in order to apply a fluid driving pressure based on a centrifugal force to the substrate.

* * * * *